United States Patent

Fujishiro et al.

[11] Patent Number: 5,991,039
[45] Date of Patent: Nov. 23, 1999

[54] ELECTRIC COMPONENT MONITORING DEVICE AND ELECTRONIC COMPONENT MONITORING METHOD

[75] Inventors: Keisuke Fujishiro; Hiroshi Murata, both of Miyaki-gun; Minehiko Goto, Chikushi-gun; Koji Takata, Fukuoka, all of Japan

[73] Assignee: Matsushita Electronic Industrial Co., Ltd., Japan

[21] Appl. No.: 08/976,450

[22] Filed: Nov. 25, 1997

[30] Foreign Application Priority Data

Nov. 27, 1996 [JP] Japan ................................. 8-315947

[51] Int. Cl.$^6$ .......................... G01B 11/14; G01N 21/55; B23K 31/12
[52] U.S. Cl. ...................... 356/375; 356/237.5; 228/105
[58] Field of Search ............................ 228/105; 356/375, 356/237

[56] References Cited

U.S. PATENT DOCUMENTS 4,677,473  6/1987  Okamoto et al. ....................... 356/376
5,601,229  2/1997  Nakazato et al. ....................... 228/246

FOREIGN PATENT DOCUMENTS 5-153997  6/1996  Japan .

Primary Examiner—Robert H. Kim
Assistant Examiner—Zandra V. Smith
Attorney, Agent, or Firm—Parkhurst & Wendel, L.L.P

[57] ABSTRACT

An electronic component monitoring device and method for correctly recognizing electronic components with bumps. A reflection-recognizing light emitter for emitting light toward an array of bumps on an electronic component, a transmission-recognizing light emitter for emitting light toward a background board, and a bump-recognizing light emitter for emitting light at an acute angle toward the array face of the electronic component are provided, and switchable light emitter(s) is/are switched on and off in accordance with a bump recognition method, transmission recognition method, and reflection recognition method.

6 Claims, 7 Drawing Sheets

☒ Bright

☐ Dark

ELECTRIC COMPONENT MONITORING DEVICE AND ELECTRONIC COMPONENT MONITORING METHOD

FIELD OF THE INVENTION

The present invention relates to the field of electronic component monitoring devices and electronic component monitoring methods suitable for monitoring electronic components with bumps.

BACKGROUND OF THE INVENTION

An improved technology for electronic component monitoring devices that rely on characteristics of electronic components with bumps has already been proposed in Japanese Laid-open patent H8-153997.

Such an electronic component monitoring device is explained with reference to FIGS. 6, 7A, and 7B.

In FIG. 6, an electronic component with bumps 1 has a molded main body 2, and a substrate 3 provided underneath the main body 2. A plurality of bumps 4 are formed in a matrix pattern on the bottom face of the substrate 3 as terminals of the electronic component with bumps 1. The bumps 4 have a semi-spherical shape and mirror-like and curved surface. Bumps 4 are preferably comprised of solder, gold or any other conductive or semicondutive material suitable as terminals.

The electronic component with bumps 1 is held by a nozzle 5 disposed at the lower part of a transfer head 6 by suction force. A background board 7 is attached to the transfer head 6 behind the electronic component with bumps 1.

A light source unit 8 having a concave area 9 on its upper part is provided below the electronic component with bumps 1. A lens-barrel 10 which runs through the center of the light source unit is provided at the lower part of the concave area 9. A camera 11 attached to the lens-barrel 10 monitors the bottom face of the electronic component with bumps 1 through the lens-barrel 10 and concave area 9.

Numerous LEDs 12, which emit light toward the bottom face (bumps 4) of the electronic component with bumps 1, are disposed on angled planes of the concave area 9. An optical fiber 14 connected to a halogen light source 13 is provided at both sides of the light source unit 8 to light-up the background board 7 from the direction of arrow marks N1 and N2 shown in FIG. 6.

As shown in FIG. 7A, bump 4 is secured on a land 15 formed on the bottom face of the substrate 3. However, in some instances a bump 4 is missing and the land 15 is exposed at the bottom face of the substrate 3, as shown by A in FIG. 7A. Such an electronic component with bumps 1 is defective, and may need to be rejected from the line.

With the electronic component monitoring device of the prior art as configured above, the land 15, which is made of a metal foil such as copper and has an even metal surface, brightly shines as a result of the emitted light.

FIG. 7B shows an image monitored by the electronic component monitoring device of the prior art as shown in FIG. 6. In FIG. 7B, shaded portions indicate bright areas, and other portions indicate dark areas. A point P1 indicates a corner 3a of the substrate 3, and images S1 and S2 are the part A in FIG. 7A.

It is apparent that there is no difference between the image S2, which corresponds to the land 15 only, and the image S1, which corresponds to a land 15 and bump 4 combination.

An image processing unit of the prior art thus erroneously judges this part which, in fact, should be designated "defective." Accordingly, the electronic component monitoring device of the prior art has low reliability in recognizing the electronic component with bumps 1. As a result, an electronic component may be mounted on a substrate at an erroneous bump position due to erroneous recognition of a wiring pattern near the land 15.

SUMMARY OF THE INVENTION

The present invention offers an electronic component monitoring device and electronic component monitoring method which are each capable of correctly recognizing electronic components with bumps.

The electronic component monitoring device of the present invention comprises a transfer head for holding an electronic component, a background board disposed at the back of the electronic component held by the transfer head, a camera for monitoring the electronic component, a reflection-recognizing light emitter for applying the light to the terminal arrayed face of the electronic component, a transmission-recognizing light emitter for applying the light to the background board, and a bump-recognizing light emitter for applying the light at an acute angle to the terminal arrayed face of the electronic component.

The electronic component monitoring method of the present invention comprises providing the reflection-recognizing light emitter, transmission-recognizing light emitter, and bump-recognizing light emitter. A light emitter to be turned on is switched among the reflection-recognizing light emitter, transmission-recognizing light emitter, and bump-recognizing light emitter in accordance with a bump recognition method, transmission recognition method, and reflection recognition method.

DESCRIPTION OF THE PREFERRED EMBODIMENTS

An exemplary embodiment of the present invention is explained with reference to figures.

Figure 1:
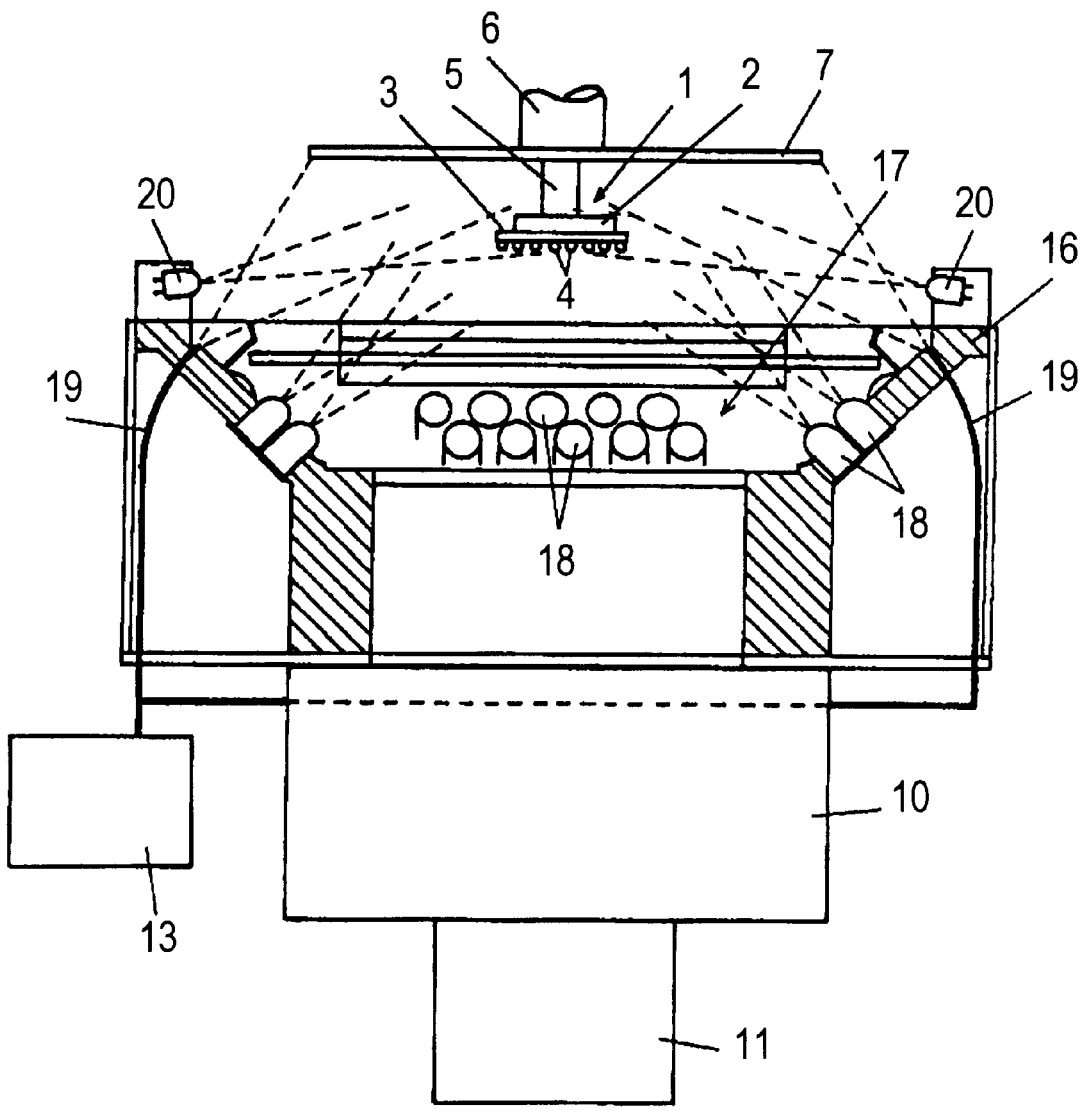
FIG. 1 is a side view of an electronic component monitoring device in accordance with an exemplary embodiment of the present invention.

FIG. 1 shows a side view of an electronic component monitoring device in an exemplary embodiment of the present invention. In FIG. 1, an electronic component with bumps 1 has a molded main body 2, and a substrate 3 provided underneath the main body 2. A plurality of bumps 4 are formed in a matrix pattern on the bottom face of the substrate 3. The bumps 4 function as terminals of the electronic component with bumps 1. The bumps 4 have a semi-spherical shape and mirror-like and curved surface. The electronic component with bumps 1 is held by a nozzle 5 disposed at the lower part of a transfer head 6 by suction force. A background board 7 is attached to the transfer head 6 behind the electronic component with bumps 1. A light source unit 16 has a concave area 17 at its upper part, and a reflection-recognizing light emitter 18 (consisting of numerous LEDs), which emits light toward the bottom face (bumps 4) of the electronic component with bumps 1, is disposed on an angled plane of the concave area 17.

A transmission-recognizing light emitter 19 (consisting of optical fibers) connected to a halogen light source 13 is disposed on an upper area of the angled plane of the concave area 17. A bump-recognizing light emitter 20, which emits light at an acute angle toward the bump array face (almost horizontal when the bump array face is horizontal) is disposed on an uppermost area of the concave area 17.

Figure 2:
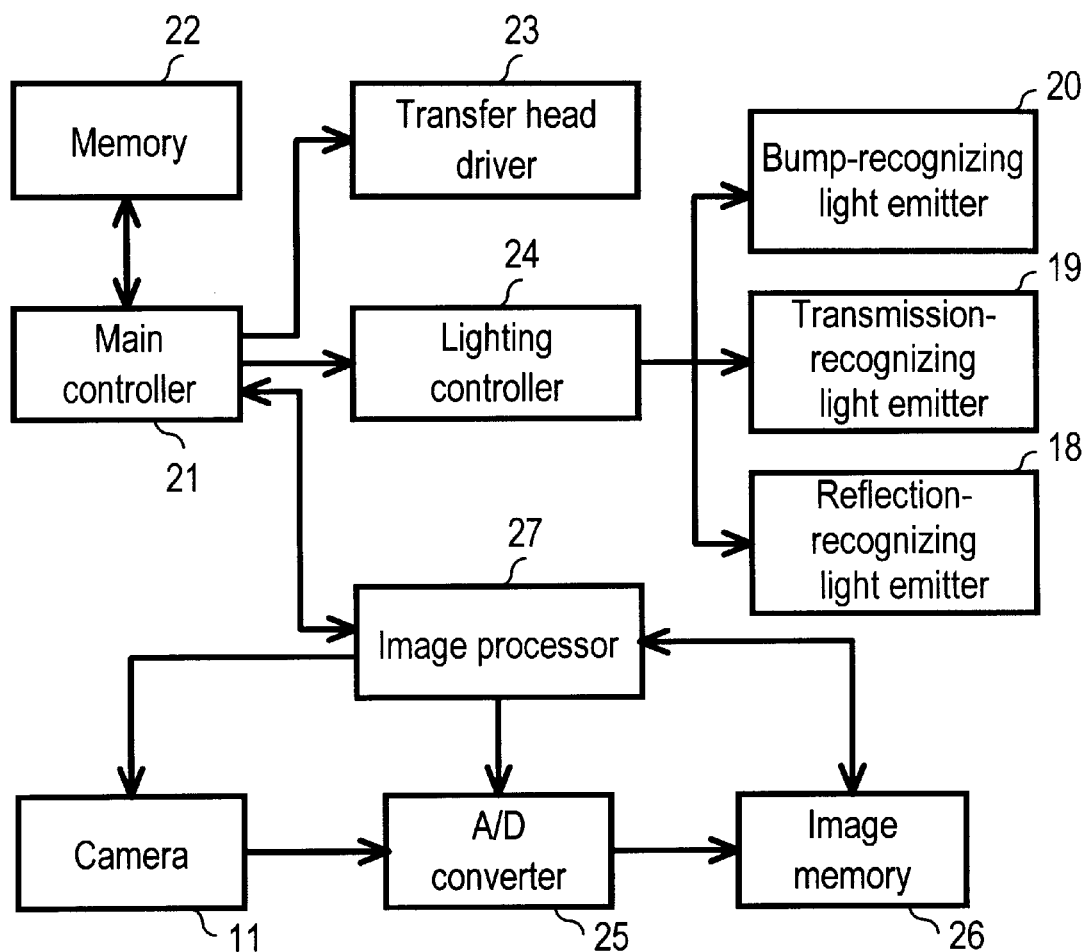
FIG. 2 is a control block diagram of the electronic component monitoring device in accordance with the exemplary embodiment of the present invention.

The reflection-recognizing light emitter 18, transmission-recognizing light emitter 19, and bump-recognizing light emitter 20 are switched in accordance with a recognition method (bump recognition method, transmission recognition method, and reflection recognition method) selected by a control block as shown in FIG. 2.

In FIG. 2, a main controller 21 controls the entire operation, a memory 22 stores data including recognition methods and shape of each electronic component, and a transfer head driver 23 drives the transfer head 6 to X, Y, z, θ directions.

A lighting controller 24 receives information on recognition methods from the main controller 21, and switches on and off each of the reflection-recognizing light emitter 18, transmission-recognizing light emitter 19, and bump-recognizing light emitter 20 as will be explained later herein.

An A/D converter 25 converts analog image information captured by the camera 11 to a digital signal, and the digital signal is stored in the image memory 26.

An image processor 27 recognizes a dislocation or an entirely missing bump 4 of the electronic component with bumps 1 based on the image received from the image memory 26, and outputs recognition results including positional information of the bump 4 and determination of "acceptable" or "unacceptable" to the main controller 21. The main controller 21 controls the transfer head driver 23 based on the recognition results for transferring an electronic component held by the transfer head 6 onto a substrate, which is not illustrated, or disposing of a defective electronic component to a specified area.

The operation of an electronic component mounter as configured above is explained with reference to FIGS. 3 and 4a–c.

In Step 1, the transfer head 6 picks up an electronic component from a feeder, which is not illustrated, and transfers the electronic component over the electronic component monitoring device. In Step 2, the recognition method suitable for the electronic component which is currently held by the nozzle 5 by suction force is obtained from the memory 22.

If the bump recognition method is selected, the lighting controller 24 turns on the bump-recognizing light emitter 20 and transmission-recognizing light emitter 19, and turns off the reflection-recognizing light emitter 18.

Here, the transmission-recognizing light emitter 19 may also be turned off. However, it is easier to identify corners of the substrate 3 in the image if both bump-recognizing light emitter 20 and transmission-recognizing light emitter 19 are turned on, thereby enabling faster recognition of a rough position of the bump 4 faster.

Figure 4A:
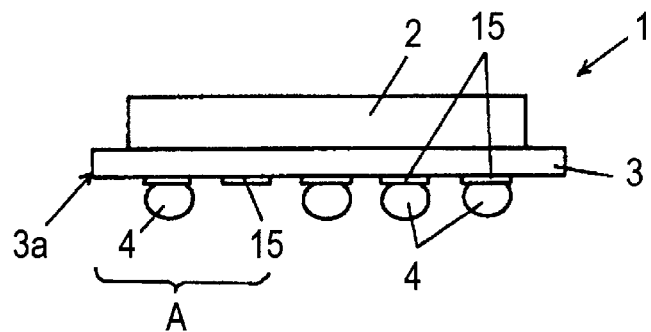
FIG. 4A is a side view of an electronic component with bumps held by the electronic component monitoring device in accordance with the exemplary embodiment of the present invention.
Figure 4B:
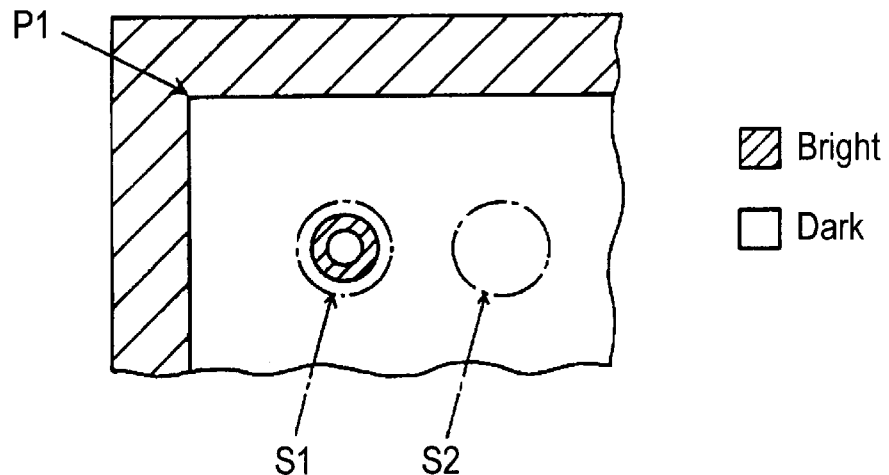
FIG. 4B is an example of an image of a part A in FIG. 4A.
Figure 7A:
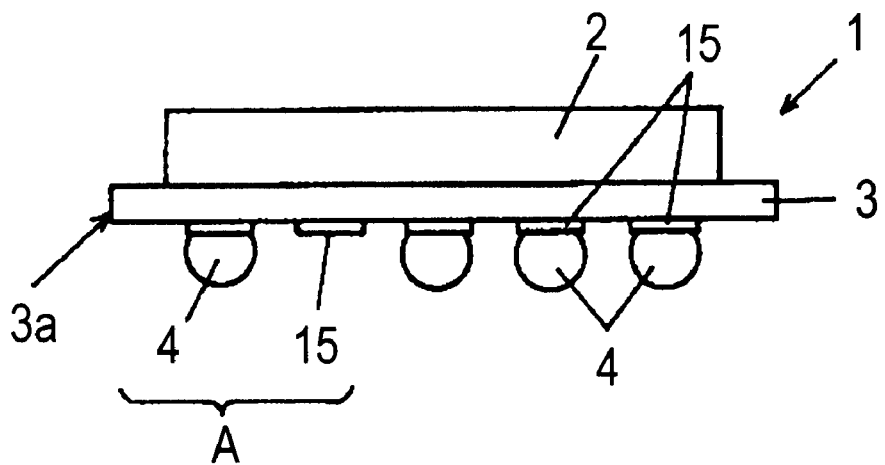
FIG. 7A is a side view of an electronic component with bumps held by the electronic component monitoring device of the prior art.
Figure 7B:
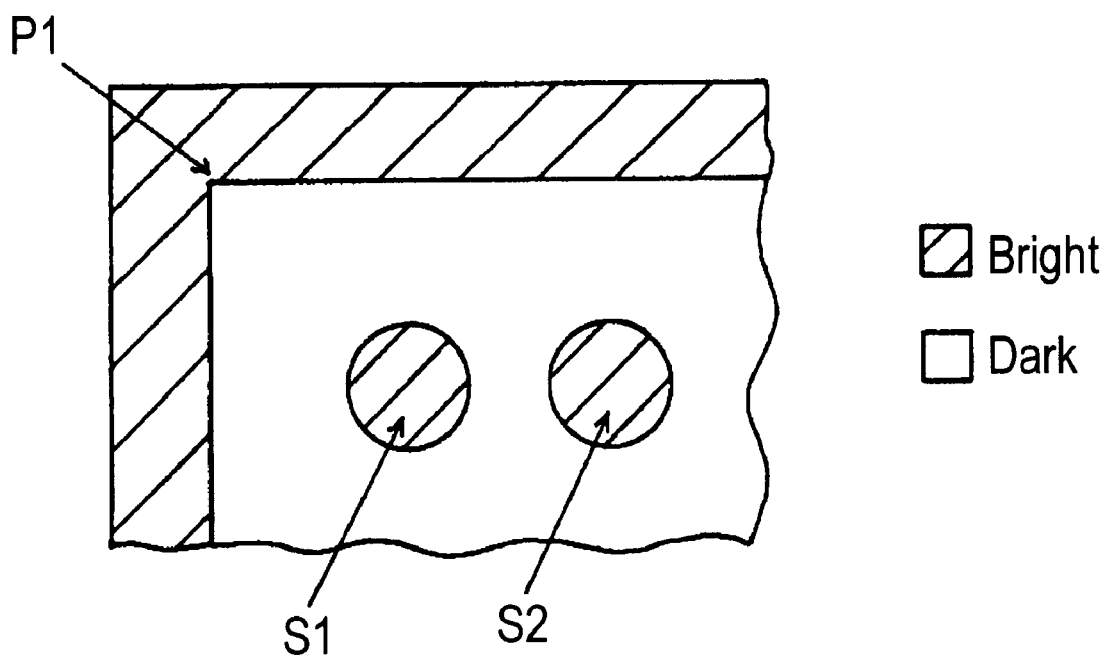
FIG. 7B is an example of an image of a part A in FIG. 7A of the electronic component monitoring device of the prior art.

The monitoring operation in accordance with the bump recognition method is explained with reference in FIGS. 4A–4C. When there is a missing bump 4 at a part A, similarly shown in FIG. 7A for the prior art, an image captured by the camera 11 will look as shown in FIG. 4B.

Specifically, at an area where the bump 4 is missing and the land 15 is exposed, the light does not reflect to the direction of the camera 11 positioned right underneath because the land 15 has an even metal surface and the bump-recognizing light emitter 20 applies the light to the bump face at an acute angle to the bump arrayed face. Accordingly, the image S2 in FIG. 4B is monitored as a dark area.

Figure 4C:
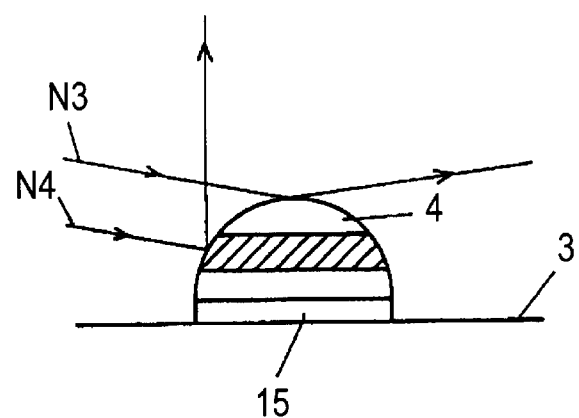
FIG. 4C is a magnified side view illustrating lightened and dark areas by applying the light to a bump in FIG. 4A.

When the bump 4 is secured on the land 15, the light emitted from the bump-recognizing light emitter 20 is reflected as shown in FIG. 4C.

Specifically, the light entering near the top of the bump 4 as indicated by an arrow N3 reflects almost parallel to the substrate 3, and does not reflect toward the camera 11. An image of the top part of the bump 4 is thus dark. However, the light entering the middle part of the bump 4 as indicated by an arrow N4 reflects almost perpendicularly to the substrate 3 towards the camera 11.

Accordingly, a ring-shaped bright image shown as the image S1 in FIG. 4B is monitored when the bump 4 exists. A ring pattern (binary or multivalued) is therefore registered to the image processor 27 for identifying the position of the bump 4 by pattern matching.

The presence of the bump 4 can thus be differentiated by the image S1 and S2 as shown in FIG. 4B. The exemplary embodiment does not erroneously determine the land 15 exposed without the bump 4 to be "acceptable," which may happen with the prior art. Thus, reliability of recognition is improved. In FIG. 4B, shaded portions indicate bright areas and others are dark areas.

Figure 3:
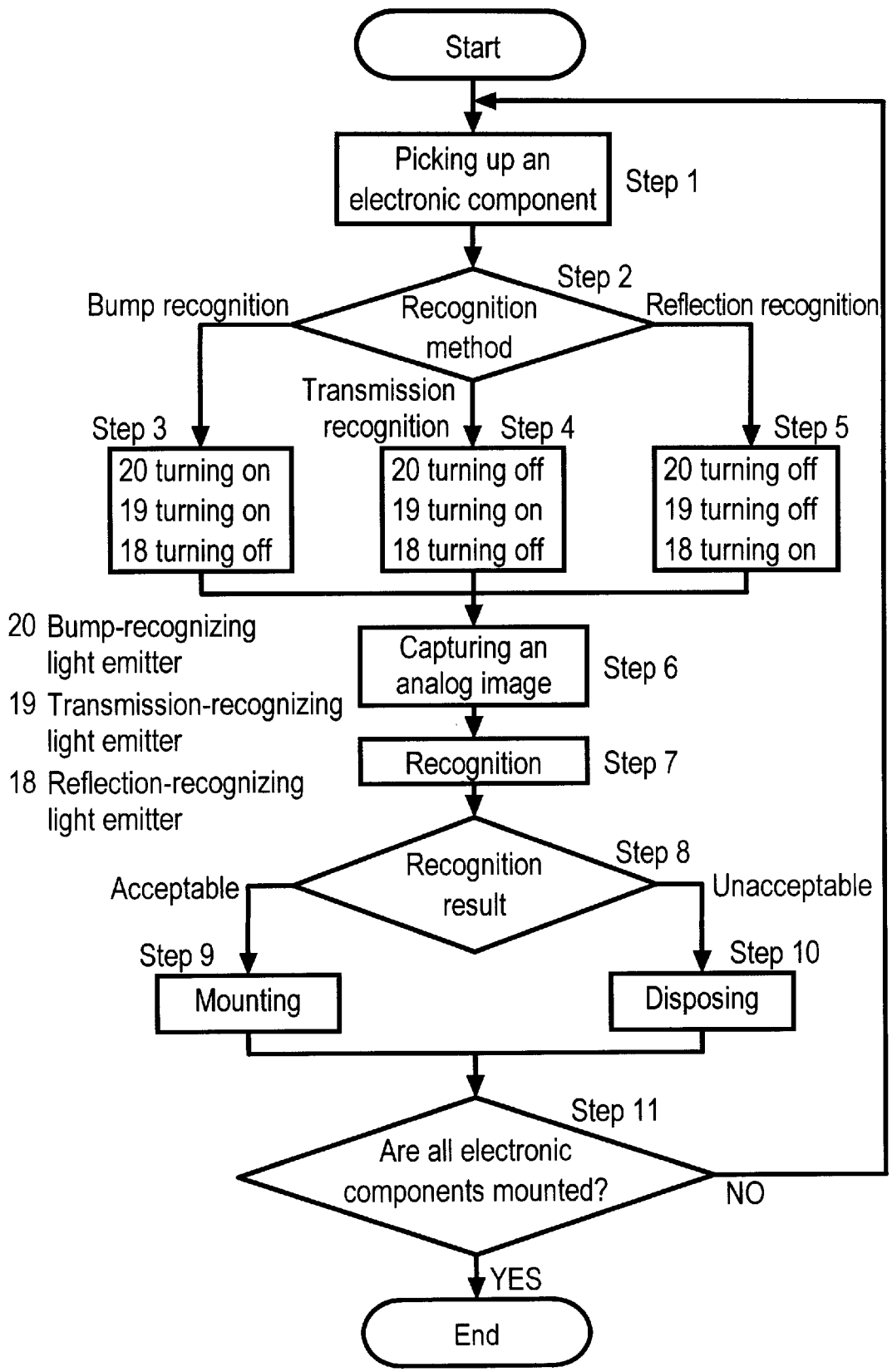
FIG. 3 is a flow chart of the electronic component monitoring device in accordance with the exemplary embodiment of the present invention.

When the transmission recognition method is selected in Step 2 in FIG. 3, only the transmission-recognizing light emitter 19 is turned on, and the reflection-recognizing light emitter 18 and bump-recognizing light emitter 20 are turned off.

Figure 5A:
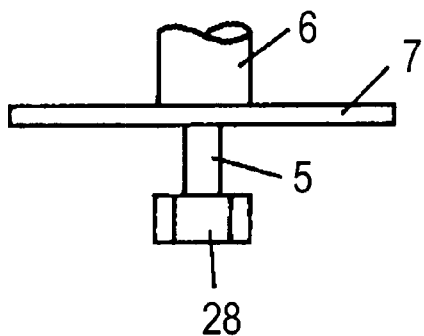
FIG. 5A is a side view of an electronic component held by the electronic component monitoring device in accordance with the exemplary embodiment of the present invention which is suitable for the transmission recognition method.

The transmission recognition method is suitable for a square chip 28, shown in FIG. 5A and electronic components with leads such as QFPs (Quad Flat Package) and SOPs (Single Outline Package).

Figure 5B:
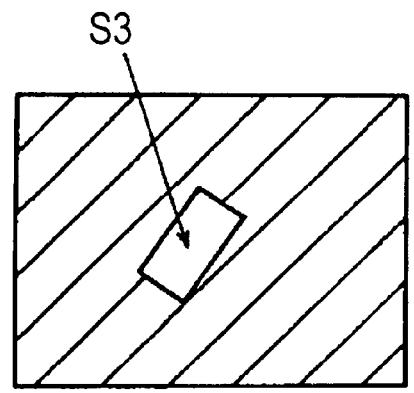
FIG. 5B is an example of an image of FIG. 5A.

When this method is selected, the background board 7 is lighted and a dark silhouette of an electronic component shown on the background board 7 is monitored as shown in FIG. 5B. In this exemplary embodiment, the background board 7 is lighted from beneath the electronic component using the transmission-recognizing light emitter 19 as shown in FIG. 1. However, the background 7 may also be lightened from over the electronic component.

When the reflection recognition method is selected in Step 2 in FIG. 3, the reflection-recognizing light emitter 18 is turned on (Step 5), and the transmission-recognizing light emitter 19 may additionally be turned on.

Figure 5C:
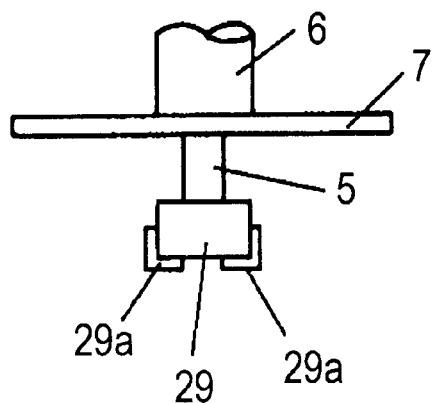
FIG. 5C is a side view of an electronic component held by the electronic component monitoring device in accordance with the exemplary embodiment of the present invention which is suitable for the reflection recognition method.
Figure 5D:
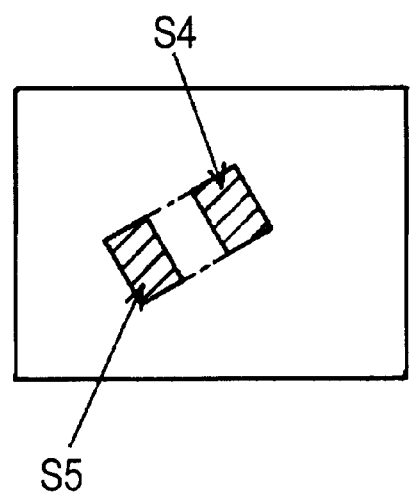
FIG. 5D is an example of an image of FIG. 5C.
Figure 6:
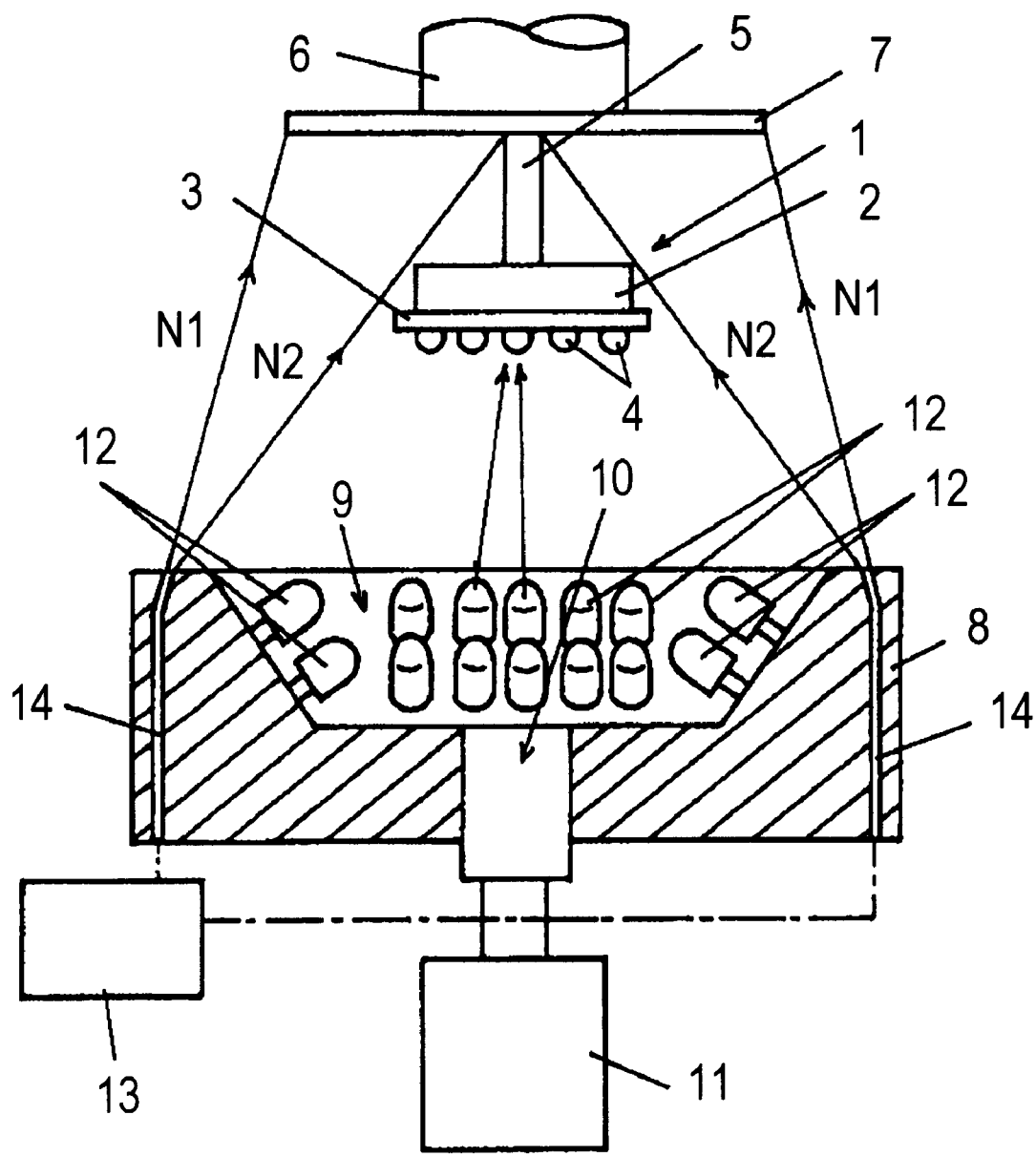
FIG. 6 is a side view of an electronic component monitoring device of the prior art.

The reflection recognition method is suitable for a J-lead component 29, as shown in FIG. 5C, which has a J-lead 29a bent inward. In this method, only the J-lead 29a is monitored as bright images S4 and S5 as shown in FIG. 5D. In FIGS. 5B and 5D, shaded portions indicate bright areas and others are dark areas.

At Step 6 in FIG. 3, an analog image captured by the camera 11 is converted to a digital image by the A/D converter 25, and the digital image is stored in the image memory 26. The image processor 27 recognizes dislocation and other points in accordance with the recognition method for each electronic component (Step 7), and a recognition result is obtained. If the recognition result is "acceptable," the electronic component is mounted on the substrate based on the detected position of the bump 4 (Step 9). If the result is "unacceptable," this electronic component is disposed of (Step 10). Whether all electronic components are mounted is confirmed (Step 11), and if there is any missing electronic component, the next electronic component is picked up, going back to Step 1, to complete the operation.

As explained above, the electronic component monitoring device of the present invention comprises a transfer head for holding the electronic component, background board disposed behind the electronic component held by the transfer head, camera for monitoring the electronic component, reflection-recognizing light emitter for emitting light toward the terminal array face of the electronic component, transmission-recognizing light emitter for emitting light toward the background board, and bump-recognizing light emitter for emitting light at an acute angle toward the terminal array face of the electronic component.

The electronic component monitoring method of the present invention employs the reflection-recognizing light emitter for emitting light toward the terminal array face of the electronic component, transmission-recognizing light emitter for emitting light toward the background board, and bump-recognizing light emitter for emitting light at an acute angle toward the terminal array face of the electronic component. These light emitters are switched according to one of the bump recognition method, transmission recognition method and reflection recognition method selected for recognizing the electronic component.

For monitoring the electronic components with bumps, the bump-recognizing light emitter is turned on. With this light emitter, a ring image is obtained if there is a bump thereby clearly differentiating an image of a land exposed without a bump. This improves the reliability of recognition by reducing erroneous recognition. For other shapes of electronic components, only the transmission-recognizing light emitter may be turned on to monitor a silhouette of the image captured by the camera. In other cases, at least the reflection-recognizing light emitter may be turned on to monitor a bright image of terminals of an electronic component in the image to recognize the shape.

The electronic component monitoring device and method of the present invention has been explained using the bump shape shown in FIG. 4C as an example. However, acute irradiation angle of the bump-recognizing light emitter to the bump face may not always be optimal if the curved shape of the bump differs. It is apparent that an irradiation angle may have to be optimized according to the shape of the bump. The exemplary embodiments described herein are therefore illustrative and not restrictive. The scope of the invention being indicated by the appended claims and all modifications which come within the true spirit of the claims are intended to be embraced therein.

What is claimed is:

1. An electronic component monitoring device, comprising:

a transfer head for holding an electronic component at a location at a distal end of said transfer head;

a background board disposed behind said transfer head and electronic component held at said location;

a reflection-recognizing light emitter for emitting light toward said location at the distal end of said transfer head and a terminal arrayed face of any electronic component held at said location by said transfer head;

a transmission-recognizing light emitter for emitting light toward said background board;

a bump-recognizing light emitter for emitting light at an acute angle toward said location at the distal end of said transfer head and for illuminating a terminal arrayed face of any electronic component at said location; and a camera for monitoring any electronic component held at said location at a distal end of said transfer head, having an axis of light substantially perpendicular to and facing the plane of a terminal arrayed face of any electronic component held at said location; and control means for recognizing a type of electronic component scanned by said camera and for selecting a suitable recognition method to monitor an electronic component based on the recognized type.

2. An electronic component monitoring device of claim 1, further comprising:

a lighting controller for switching on and off said reflection-recognizing light emitter, said transmission-recognizing light emitter, and said bump-recognizing light emitter simultaneously based on a recognition method selected by said control means.

3. An electronic component monitoring method employing an electronic component monitoring device, comprising the steps of:

providing a transfer head for holding an electronic component at a location at a distal end of said transfer head;

providing a background board disposed behind said transfer head and said electronic component held at said location;

providing a camera for monitoring an electronic component held at said location at a distal end of said transfer head, having an axis of light substantially perpendicular to and facing the plane of a terminal arrayed face of any electronic component held at said location;

providing control means for recognizing a type of electronic component scanned by said camera and for selecting a suitable recognition method to monitor an electronic component based on the recognized type; and monitoring an electronic component held at said location by said transfer head by switching on and off in a predetermined pattern at least one of (i) a reflection-recognizing light emitter for emitting light toward said location at a distal end of said transfer head for illuminating a terminal arrayed face of any electronic component held at said location, (ii) a transmission-recognizing light emitter for emitting light toward said background board, and (iii) a bump-recognizing light emitter for emitting light at an acute angle toward said plane for illuminating a terminal arrayed face of any electronic component held at said location.

4. An electronic component monitoring method as defined in claim 3, wherein at least said bump-recognizing light emitter is turned on and light therefrom is used for differentiating between an area of an electronic component with a bump and an area of an electronic component without a bump in an image captured by the camera.

5. An electronic component monitoring method as defined in claim 3, wherein only said transmission-recognizing light emitter is turned on and light therefrom is used for monitoring based on a silhouette image captured by said camera of a shape of an electronic component held by said transfer head.

6. An electronic component monitoring method as defined in claim 3, wherein at least said reflection-recognizing light emitter is turned on to obtain in an image captured by the camera a bright image only for terminals of an electronic component held at said location.

* * * * *